United States Patent
Jussel et al.

(10) Patent No.: US 7,534,028 B2
(45) Date of Patent: May 19, 2009

(54) BURNING OVEN

(75) Inventors: Rudolf Jussel, Feldkirch-Tosters (AT);
Heinrich K. Feichtinger, Hinteregg (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 11/153,782

(22) Filed: Jun. 15, 2005

(65) Prior Publication Data

US 2006/0088077 A1    Apr. 27, 2006

(30) Foreign Application Priority Data

Oct. 21, 2004  (DE) .................. 10 2004 051 409

(51) Int. Cl.
*G01K 15/00* (2006.01)
*G01K 11/06* (2006.01)

(52) U.S. Cl. .................... 374/1; 374/141; 374/160; 374/179

(58) Field of Classification Search .......... 374/31, 374/36, 38, 1–2, 141, 144, 148, 10–12, 20, 374/129, 30, 137, 179, 160, 163, 183; 219/201; 432/120

See application file for complete search history.

(56) References Cited

U.S. PATENT DOCUMENTS

| 1,869,831 | A | * | 8/1932 | Thompson | 219/409 |
|---|---|---|---|---|---|
| 2,398,874 | A | * | 4/1946 | Weyhing | 219/390 |
| 3,181,847 | A | * | 5/1965 | Hauth, Jr. et al. | 432/3 |
| 3,393,562 | A | * | 7/1968 | Breedlove | 374/37 |
| 3,800,716 | A | * | 4/1974 | Berger | 110/173 R |
| 4,565,788 | A | * | 1/1986 | Milovidov et al. | 436/137 |
| 4,761,539 | A | * | 8/1988 | Carmean | 219/497 |
| 4,923,681 | A | * | 5/1990 | Cox et al. | 422/116 |
| 5,265,957 | A | * | 11/1993 | Moslehi et al. | 374/1 |
| 5,326,170 | A | * | 7/1994 | Moslehi et al. | 374/2 |
| 5,375,187 | A | * | 12/1994 | Ibsen et al. | 392/416 |
| 5,707,147 | A | * | 1/1998 | Kurkowski et al. | 374/1 |
| 5,938,962 | A | * | 8/1999 | Adamski et al. | 219/502 |
| 6,329,643 | B1 | * | 12/2001 | Suzuki et al. | 219/497 |
| 6,398,405 | B1 | * | 6/2002 | Yamada | 374/1 |
| 6,561,694 | B1 | * | 5/2003 | Lerch et al. | 374/126 |
| 6,769,803 | B1 | * | 8/2004 | Feichtinger et al. | 374/1 |
| 7,063,457 | B2 | * | 6/2006 | Kang et al. | 374/3 |
| 2004/0247013 | A1 | * | 12/2004 | Clark et al. | 374/1 |
| 2007/0195853 | A1 | * | 8/2007 | Park et al. | 374/1 |
| 2007/0291816 | A1 | * | 12/2007 | Volf et al. | 374/1 |
| 2008/0013591 | A1 | * | 1/2008 | Kim et al. | 374/1 |

FOREIGN PATENT DOCUMENTS

| DE | 42 18 032 A1 | | 1/1993 |
| DE | 42 06 540 A1 | | 9/1993 |
| DE | 19831451 A1 | * | 1/2000 |
| JP | 02168131 A | * | 6/1990 |
| SU | 513273 | | 5/1973 |

* cited by examiner

*Primary Examiner*—Gail Verbitsky
(74) *Attorney, Agent, or Firm*—John C. Thompson; Alan S. Korman

(57) ABSTRACT

A burning oven, especially for dental materials, is provided and includes a temperature detection element and a calibrating device for calibrating the temperature detection element. The calibrating device has a temperature sensor that in turn can be calibrated at a given number of temperature points, especially one or two temperature points.

9 Claims, 4 Drawing Sheets

BURNING OVEN

CROSS-REFERENCE TO RELATED APPLICATIONS

This application claims foreign priority benefits under 35 U.S.C. §119 from German patent application Ser. No. 10 2004 051 409.7 filed Oct. 21, 2004.

TECHNICAL FIELD

The present invention relates generally to a burning oven or kiln, especially for dental materials, and more particularly to such an oven or kiln which has a temperature detection element and a also calibration device for calibrating the temperature detection element.

BACKGROUND OF THE INVENTION

Burning ovens of this type have been known for a long time. It is important for burning ovens, for example for dental ceramics, to be calibrated, since the restoration result that can be achieved depends greatly upon the extent to which the temperature curve started pursuant to the pertinent burning program is in actuality maintained. In practice, an incorrect calibration can very readily lead to a temperature error of 10° C., which is unacceptable.

So-called silver melt probes have been used for a long time to calibrate burn ovens. Silver typically melts exactly at the temperature of 961.3° C. With the manual silver melt probe, a holder is centrally placed in the burning oven for a horizontally arranged silver wire that is connected on one side. The melting of the silver wire leads to the lowering of the horizontal position of the silver wire and is effected precisely at this temperature point. The dental technician that recalibrates the burning oven adjusts the burning oven so that at this temperature point, the reference temperature, the burning oven indicates precisely 961.3° C.

At greater deviations, however, it is necessary to recalibrate by repeating the manual calibration. In addition, although the process is quite simple, it frequently suffers from errors. For example, the silver probe must not be placed upon a honeycombed support, since this would falsify the measurement result. Furthermore, the silver probe must be positioned exactly in the middle of the oven base in order to enable a reliable reference. Finally, the beginning of the melting depends upon the subjective observation of the dental technician. Furthermore, it is also important that the calibration not be undertaken immediately after a burning process or when the burning oven is cold, since in the first instance the starting temperature is too high and in the second instance the starting temperature would be too low.

Due to these drawbacks, it has been known for a long time to automate the calibration of an oven. For example, DE 4218 032 A1 discloses an oven for carrying out thermal analyses, whereby the temperature of the oven support can be measured by thermocouple elements. The connection wires or leads of the thermocouple elements are guided to the outside.

DE-OS 42 06 540 furthermore discloses the use of a reference temperature element. By means of an electronic evaluation circuit, the actual temperature can be detected, and a separate calibration is desired. However, this approach is very complicated and is in particular dependent upon the precision of the evaluation. In practice a correction signal is derived based upon the melting temperature of tin (231° C.), with this correction signal being intended to permanently correct the thermocouple element located there. To this extent, no independent calibration is effected, but rather a continuous readjustment during the measurement.

The precision of the temperature measurement of all of the known calibration processes could be improved. Therefore, it is recommended in various situations that the entire burning oven be recalibrated at the factory, which of course means a corresponding expense for shipment, but also a down time in the dental technician laboratory during the calibration in the factory and the transport time.

A further problem is the deviation of the temperature profile actually realized by the burning oven from the actual temperatures that are to be maintained. In order to compensate for this drawback, it is known from DE 100 08 603 C2 to use two reference temperatures, namely the melting point of gold (1064.67° C.) and of silver (961.3° C.). In so doing, not only can an actual offset, but also a slope of the error curve, be taken into account. However, the use of two melt wires requires a very complicated process, especially since due to the different materials used one must also avoid the occurrence of contaminations.

Contaminations at the temperature detection element that is commonly used for the temperature control of the oven, which element can also be designated as a control thermocouple element, may also lead to temperature deviations. Due to vapor given off by the material being burned, the temperature detection element can become contaminated, resulting in a temperature deviation. This then requires a special, careful recalibration in order to avoid a very expensive replacement of this control thermocouple element.

It is an object of the present invention to provide a burning oven of the aforementioned general type that has a reliable calibrating step that is not susceptible to error should be possible at relatively low expense.

OBJECTS AND SUMMARY OF THE INVENTION

This object is realized pursuant to the present application by a burning oven where the calibrating device has a temperature sensor that in turn is adapted to be calibrated at a given number of temperature points, in particular one or two temperature points.

The inventive burning oven is characterized by a special temperature sensor in the calibrating device. A temperature sensor permits the calibration of the temperature detection element over the entire measurement range, in other words not only at one or two temperature points. Pursuant to the invention, the temperature sensor itself is, however, calibrated at a discrete number of temperature points, such as, for example, at two temperature points. However, the sensor preferably has an adequate linearity, especially since in an advantageous embodiment during operation it is not subjected to permanent vapors from heated-up material that is to be burned or the like. The temperature sensor can therefore be used considerably more precisely than with the heretofore known approaches for the calibration of the temperature detection element, for example also at temperatures that significantly differ from the melting temperatures of silver and gold.

Pursuant to the present invention, it is expedient that the inventive temperature sensor already provide an exact temperature profile as a reference after it itself is calibrated. The calibration of the temperature sensor can basically be effected in the sense of a recalibration during the calibration; however, it is preferable that the temperature sensor be calibrated to begin with, and in the calibration step merely an adaptation of the temperature profile of the burning oven to the desired temperature profile is undertaken.

Pursuant to the invention, it is expedient if the latent heat is used during the melting of the reference material for the temperature detection. For this purpose, the mass of the material or the substance is utilized, and via the heating-up it is established by a measuring electronic when a temperature plateau is obtained despite a uniformly supplied heating energy. This temperature plateau corresponds exactly to the melting temperature, since the heat of melting or latent heat occurs precisely at the melting point of the material.

This inventive measure makes it possible for the first time, instead of "lost" reference materials, to be able to rely on reusable reference materials. It is also possible to accommodate material in a nearly or entirely closed space in the calibrating device, so that there need be no fear of contamination due to influences from the outside upon the reference material.

Whereas pursuant to the invention the heating up is instituted as a reference temperature profile, it is to be understood that the same tendency of the temperature profile to be maintained during the melting point of the reference material can also be utilized as the reference temperature point.

Pursuant to an advantageous embodiment, it is also possible, for example, to use three small melting crucibles, which are respectively filled, for example, with aluminum, silver and gold, as reference materials, and in so doing to use three temperature points for the calibration of the calibrating device itself.

Even though a fixed installation of the inventive calibrating device in a burning oven is readily possible, it is to be understood that in larger dental laboratories merely one inventive calibrating device would suffice with which it is then possible to successively calibrate the various burning ovens. Pursuant to the invention, the term burning oven is to be understood to include not only unpressurized but also so-called pressure ovens, in other words, burning ovens where during the burning pressure is applied to the dental ceramic. Pursuant to the invention, it is particularly expedient if the temperature profile of the inventive temperature sensor—after its calibration—be fixed in the interior of the burning oven independently of the pressure, so that an adjustment of the actual temperature profile to the desired temperature profile can also be effected under pressure, and to this extent an even more precise adjustment is possible.

Pursuant to an advantageous embodiment of the inventive burning oven, at least one of the temperature points is a melting point of an essentially pure material, especially a metal, and the latent heat of the material is utilized for the temperature detection.

Pursuant to an advantageous embodiment of the inventive burning oven, the temperature sensor is in contact, especially over a large surface area, with a material that upon reaching a temperature point changes its aggregate state.

Pursuant to an advantageous embodiment of the inventive burning oven, the material, especially silver, is accommodated in a recess in the temperature sensor.

Pursuant to an advantageous embodiment of the inventive burning oven, the temperature of a material at which it changes it aggregate state, especially of silver at 961.3° C., is prescribed as a calibration temperature point. Pursuant to an advantageous embodiment of the inventive burning oven, the material that at a temperature point changes its aggregate state, is provided in a mass that is at least 10%, especially at least 30%, and preferably approximately half, of the mass of the temperature sensor.

Pursuant to an advantageous embodiment of the inventive burning oven, the burning oven is provided with an oven hood and an oven base, and the calibrating device with the temperature sensor is disposed approximately centrally in the middle, especially on the oven base, and can be removed from there.

Pursuant to an advantageous embodiment of the inventive burning oven, the temperature detecting element is disposed in the oven hood, especially in the upper portion of a combustion chamber.

Pursuant to an advantageous embodiment of the inventive burning oven, the temperature detection element is disposed in a combustion chamber of the oven above the calibrating device.

Pursuant to an advantageous embodiment of the inventive burning oven, an in particular automatic adjustment device is provided in the burning oven via which the calibrating device adjusts the temperature detection element at a plurality of temperatures.

Pursuant to an advantageous embodiment of the inventive burning oven, the temperature sensor, by the calibration via the prescribed number of temperature points, experiences an offset that can be stored until the next calibration.

Pursuant to an advantageous embodiment of the inventive burning oven, the calibrating device for the temperature detection element has stored a prescribed temperature profile for its calibration, and the calibration via the calibrating device is effected while starting a DIN temperature profile, once with underpressure and once without underpressure.

Pursuant to an advantageous embodiment of the inventive burning oven, the calibrating device is fixedly installed in the burning oven, especially in the region of the oven base.

Pursuant to an advantageous embodiment of the inventive burning oven, the calibrating device can be mounted in an insertable manner on the burning oven, and after insertion projects into the combustion chamber.

Pursuant to an advantageous embodiment of the inventive burning oven, the calibrating device is movably mounted in or on the burning oven, especially via a gooseneck or a flexible metal hose.

Pursuant to an advantageous embodiment of the inventive burning oven, the calibrating device is embodied as a retrofittable device for a burning oven.

BRIEF DESCRIPTION OF THE FIGURES

Further specific features of the present invention will be described in detail in the following description in conjunction with the accompanying schematic drawings, in which.

DESCRIPTION OF SPECIFIC EMBODIMENTS

Figure 1:
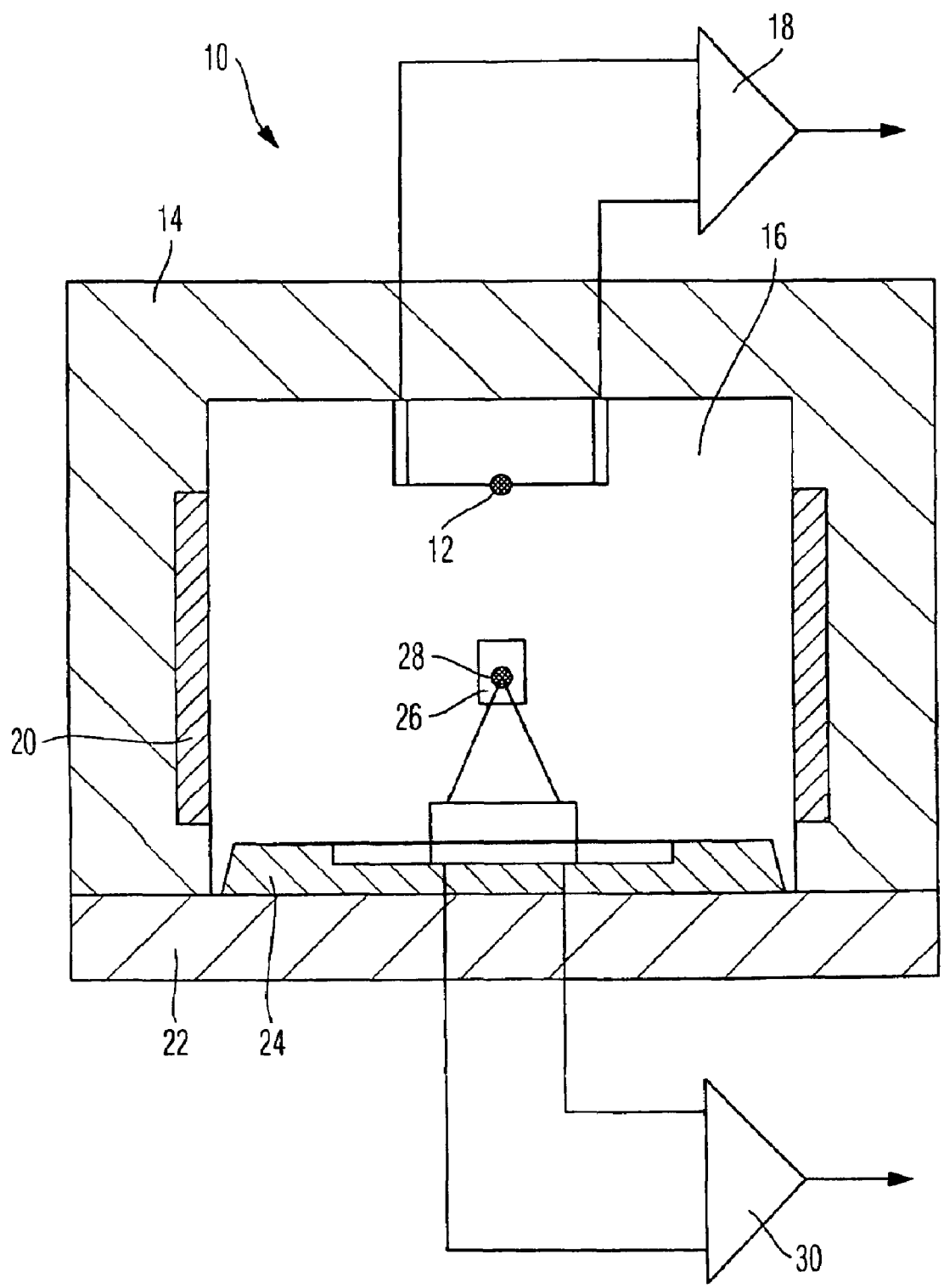
FIG. 1 is a schematic view of one exemplary embodiment of an inventive burning oven.

An inventive burning oven or kiln 10 is provided with a temperature detection element 12 that is disposed in an oven hood 14 in the upper region of a combustion chamber 16. The temperature detection element 12 serves as a control thermocouple element and controls the temperature of the burning oven during operation. For this purpose, a schematically illustrated measurement amplifier 18 is provided in the burning oven, via which the balancing or adjustment between desired temperature and actual temperature is undertaken pursuant to the measurement of the temperature detection element 12.

In a manner known per se, the oven hood 14 is provided with a heating element 20 and can be raised from an oven base 22. The oven base has a support plate 24 onto which the material that is to be burned can be placed, for example in a box, as has been known for a long time.

Instead of the arrangement illustrated in FIG. 1, the temperature detection element 12 can also be disposed on the oven base 22 or at least in the neighborhood thereof.

Pursuant to the invention, a calibrating device 26 is provided there for calibrating the oven. The calibrating device 26 is provided with a temperature probe or sensor 28 that is embodied in a special manner. The temperature sensor 28 is electrically connected with a balancing or adjustment device 30 that is part of an evaluation electronics, via which the calibration of the temperature detection element 12 is undertaken based upon the temperatures measured by the temperature sensor 28.

Figure 2:
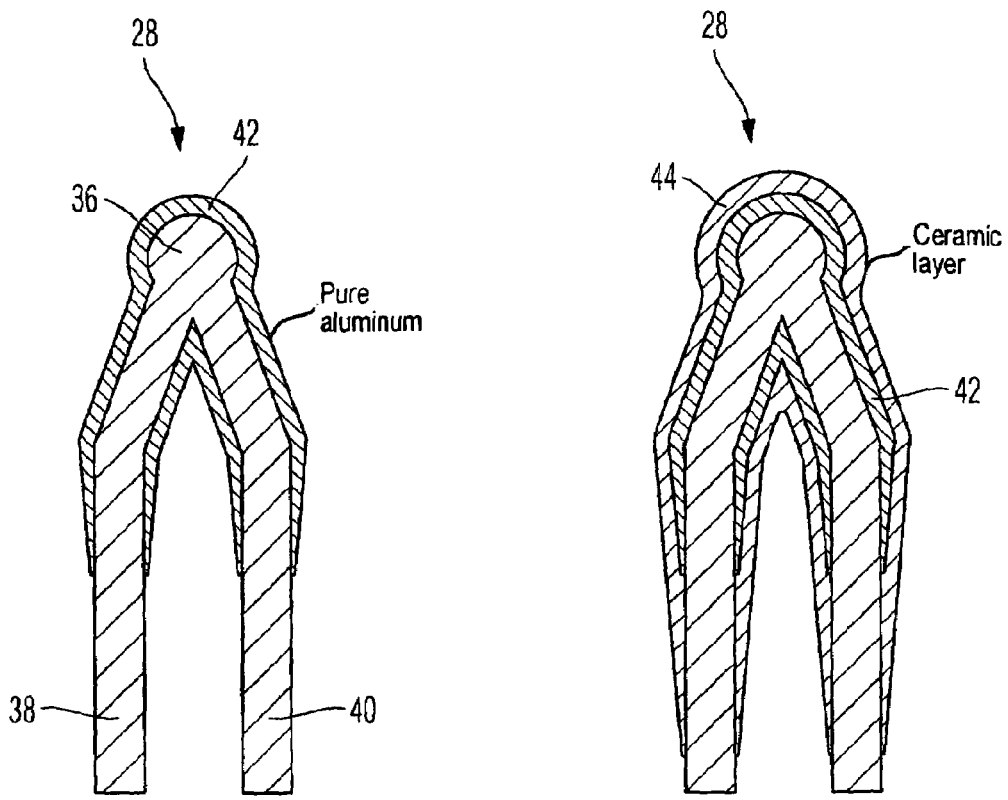
FIG. 2 is a view of the inventive temperature sensor for an inventive calibrating device for the burning oven of FIG. 1.

FIG. 2 shows two embodiments of an inventive temperature sensor. In the embodiment illustrated on the left, the temperature sensor 28 has a thermocouple 36 to form a thermocouple element. The thermocouple 36 and the adjacent portion of the pertaining connecting wires or leads 38 and 40 are completely encased by pure aluminum, and in particular in a significant quantity that, for example, can also be greater than the mass of the thermocouple itself.

A modified embodiment of the inventive temperature sensor 28 is illustrated to the right in FIG. 2. Here, the substance 42, as a reference material, is surrounded by a ceramic layer 44 that shields the reference material 42 from environmental influences. The space that accommodates the substance 42 is preferably a closed space. The reference material is selected from the group consisting of silver, aluminum, gold, magnesium, and zinc.

With the embodiment of FIG. 2, the reference material 42 or the reference substance is provided in a closed space. This precludes a conversion of the aggregate state that is affected by an oxidation or chemical conversion; rather, it is particularly expedient if the reference material is surrounded by a chemically inert layer, such as, for example, the ceramic layer 44 that is realized in the right hand portion in FIG. 2.

It is also expedient for a layer build-up to be provided for the reference material if the latter is accommodated in a closed space. Typically, a significant increase in volume of the reference material 42 occurs during the transition between the solid and the liquid aggregate state. Due to the relatively thin layer build-up in the embodiment shown at the right in FIG. 2, there is, however, ensured that the materials that are surrounded, such as the leads 38, 40 and the thermocouple 36, but also the ceramic layer 44, are not subjected to great thermal stresses.

As the reference material, any desired suitable material can be considered that has a significant latent heat and a distinct melting point, such as, for example, pure aluminum or silver.

Figure 3:
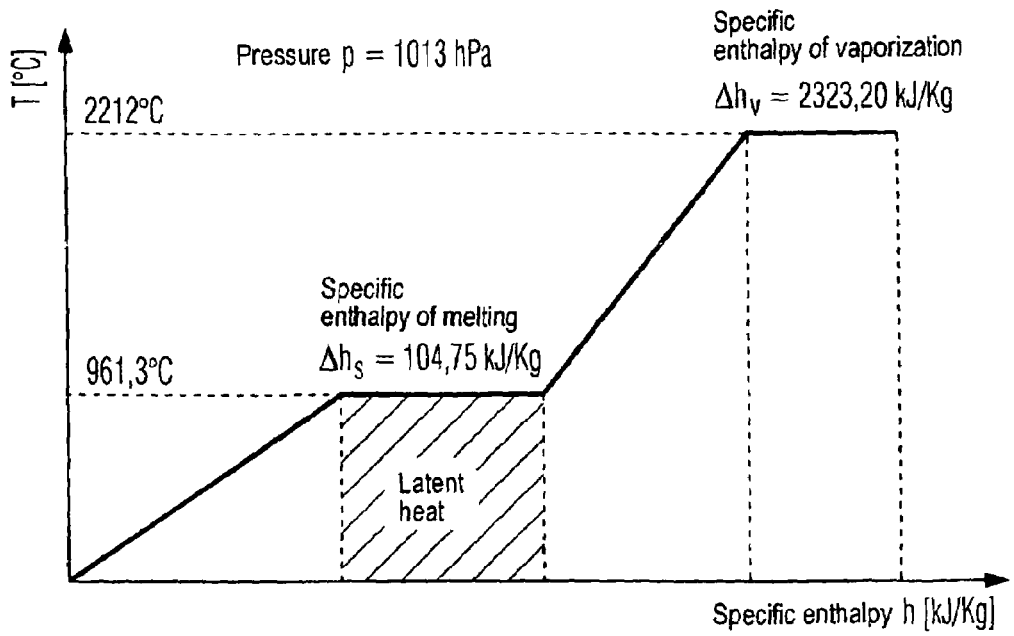
FIG. 3 is a schematic illustration of a temperature profile of a reference material (silver)

Pursuant to the invention, the heat of fusion or latent heat of the substance 42 is utilized to undertake a calibration of the inventive temperature sensor. The underlying scheme can be seen from FIG. 3 for silver as the reference material. In FIG. 3, the temperature T is plotted against the specific enthalpy h. As can be seen, below the melting temperature of 961.3° C., the temperature T increases as thermal energy is supplied. For the melting of the substance 42, the heat of fusion must be applied, which for silver is 104.75 kJ/kg. Only after the conclusion of the melting process, with the supply of heat remaining the same, does the temperature rise further, as can be seen from FIG. 3, and in particular up to the boiling point at 2212° C.

The aforementioned temperature points exist when an atmospheric pressure (1013 hPa) is provided, so that the calibration of the inventive temperature sensor is to be carried out at ambient pressure.

Figure 4:
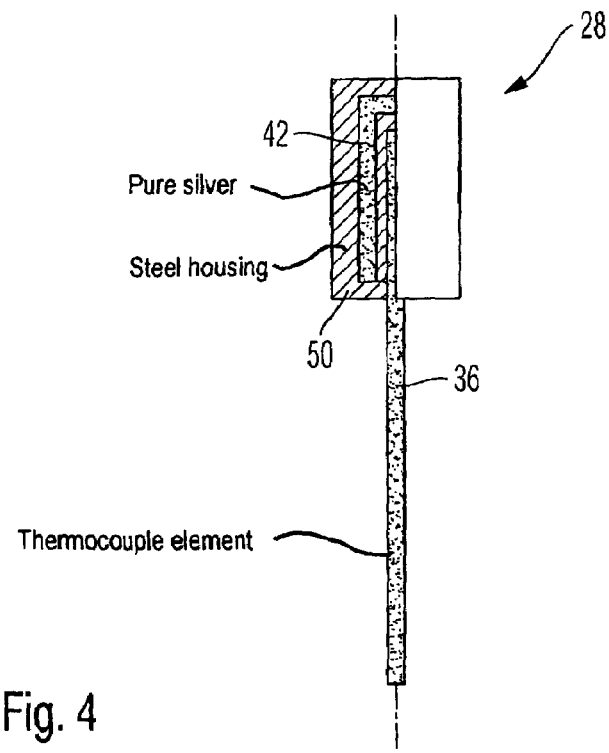
FIG. 4 is a modified embodiment of a temperature sensor for the inventive burning oven.

FIG. 4 shows a modified embodiment of an inventive temperature sensor 28. Here, pure silver, as the substance 42, is accommodated in a closed steel housing 50. For this purpose, the housing has an appropriately shaped recess. The silver 42 surrounds the thermocouple element 36 located there in a cup-shaped and closely adjacent manner, so that the enthalpy of melting has a distinct affect upon the increase in temperature of the thermocouple element 36.

This encased embodiment of the inventive temperature sensor 28 has the advantage that a complete non-dependence upon environmental influences results, whereby it is to be understood that it must be ensured by suitable measures that the increase in volume of the substance 42 during the melting not be allowed to lead to destruction of the inventive temperature sensor 28. This can be ensured, for example, by a small recess filled with nitrogen, thereby enabling at that location a spreading or displacement of the reference material when the volume increases.

Figure 5:
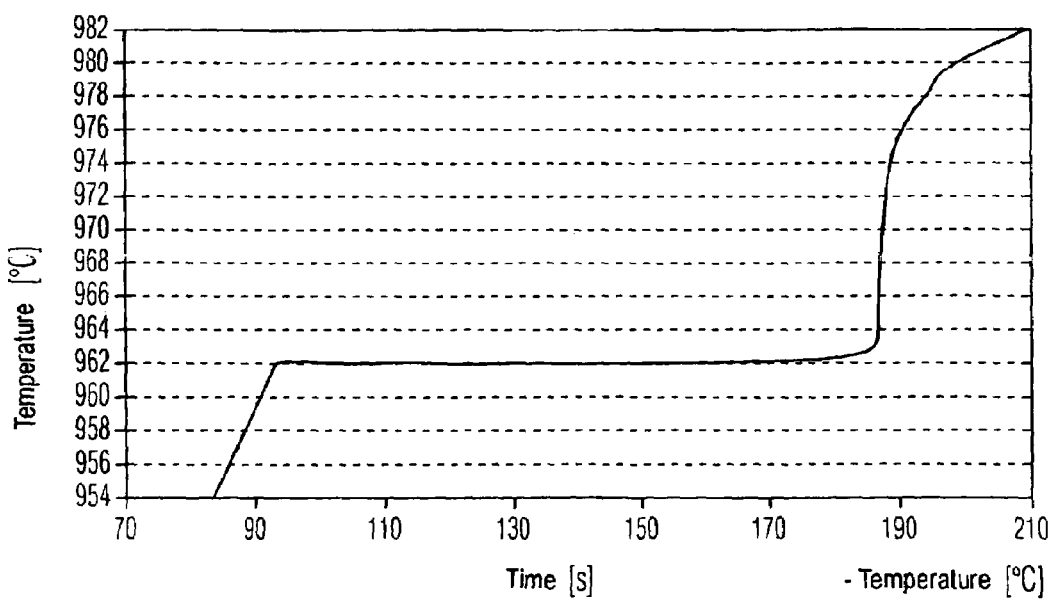
FIG. 5 shows the measured temperature profile at uniform supply of heat for an inventive temperature sensor.

From FIG. 5 it can be seen how the enthalpy of melting, or the influence of the latent heat, at a constant supply of heat, has an influence during the calibration of the inventive temperature sensor 28. The heating up of the burning oven is initially effected—below 960° C.—essentially linearly within about 90 seconds. While the supply of heat during the further course of temperature measurement of the thermocouple element 36 is not adjusted, the temperature remains essentially constant between about 95 seconds and 170 seconds, counted from the beginning of the calibration cycle. During this time period, the substance 42 melts. However, the reference thermocouple element 36 does not measure for instance the inner temperature of the combustion chamber—which increases further—but rather basically the temperature of the substance 42. In so doing, there results a temperature plateau at approximately 962° C. whereby after approximately 185 seconds the substance 42 is completely melted. There is then effected a nearly abrupt temperature increase due to the high difference of the inner temperature of the thermocouple sensor 28 and its outer temperature—the steel housing 50 has, during this time period, already heated up to a considerably higher temperature.

Figure 6:
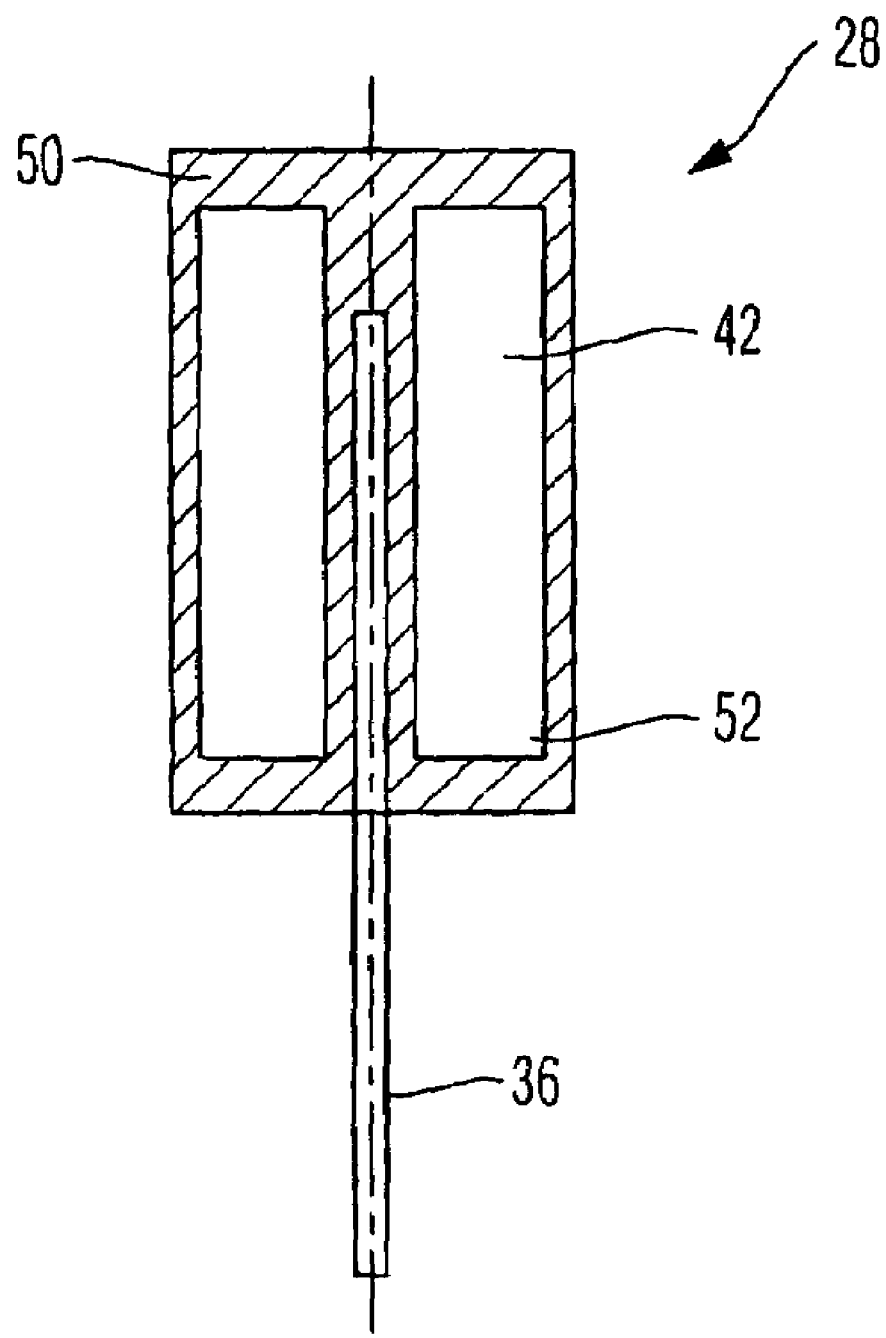
FIG. 6 is a schematic illustration of a further modified embodiment of a temperature sensor for the inventive burning oven.

A further modified embodiment of an inventive temperature sensor is shown in FIG. 6. This embodiment has certain parallels to the embodiment of the temperature sensor 28 of FIG. 4. With this embodiment, an annular chamber 52 is provided that surrounds the thermocouple element 36 in a ring-shaped manner similar to a cylinder, and in particular especially in the region of the thermocouple. The annular chamber 52 is provided in a housing 50 of solid steel, and is filled with a suitable reference material 42. The steel housing 50 actually hermetically surrounds the annular chamber 52. However, beyond the annular chamber 52 it has relatively thin walls. For example, the thickness of the steel housing 50 at this location is merely one tenth to one half, preferably approximately one third, of the thickness of the annular chamber 52. Thickness in this context means the extension or dimension in the radial direction.

With this embodiment, a considerable amount of reference material 42 can be accommodated directly adjacent to the thermocouple 36. In particular in a hermetically sealed manner, yet nevertheless without the danger that the increase in volume will burst the surrounding housing. This is based on the ability of the region of the steel housing 50 that surrounds the annular chamber 52 to expand if necessary.

The height extension of the annular chamber 52 can be selected in any suitable manner. With the embodiment illustrated in FIG. 6, the annular chamber 52 extends beyond the thermocouple 36, and extends over significantly more than half of the height of the steel housing 50. This provides a considerable volume for the reference material 42, whereby it is to be understood that the quantity that is to be used can be adapted in any desired manner to the requirements.

The reaching of the temperature plateau described here is detected by the measurement electronics, and is utilized as the reference temperature for the calibration of the temperature sensor 28. With a temperature sensor calibrated in this fashion, the temperature detection element 12 is now calibrated—preferably in a separate calibrating cycle of the inventive burning oven—and in particular with a plurality of measurement points between the lower end of the measurement region and the upper end of the measurement region of the temperature detection element 12.

Whereas the calibration has here been described with one temperature point and with the availability of one substance 42, it is to be understood that in place thereof it would also be possible to use two or more reference materials and temperature points for the calibration of the inventive temperature sensor. In this embodiment, not only can the offset of the actual temperature profile be compensated, but also the slope of the curve of the temperature profile, thereby further improving the calibration of the calibrating device.

The specification incorporates by reference the disclosure of German priority document 10 2004 051 409.7.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A burning oven comprising:
   a combustion chamber (16) formed by an oven hood (14) for the firing of dental restorations;
   an oven base (22) below the combustion chamber;
   a temperature detection element (12) disposed in said oven hood; and
   a reusable calibrating device (26) for calibrating said temperature detection element, wherein said calibrating device has a temperature sensor (28) that is calibrated at a given number of temperature points, the calibrating device further including an essentially pure substance surrounding the sensor, and a further material that at least partially surrounds a portion of the temperature sensor, wherein said essentially pure substance is disposed at least in a closed space formed between said temperature sensor (28) and said further material, the further material completely surrounding said substance, and the calibrating device being fixedly installed in said burning oven (10) in the region of the oven base, said calibrating device (26) having a stored prescribed temperature profile for calibration of said temperature detection element (12), and wherein said calibration via said calibrating device is effected while starting a temperature profile, one time with overpressure or underpressure, and one time at ambient air pressure, wherein at least one of said temperature points is a melting point of an essentially pure substance (42) that upon reaching its melting point changes its aggregate state, and wherein the temperature of said essentially pure substance, which remains constant during the duration of the aggregate state change, is utilized for the temperature detection, and wherein said temperature sensor (28) is a thermocouple.

2. A burning oven according to claim 1, wherein said given number of temperature points is either one or two temperature points.

3. A burning oven according to claim 1, wherein said essentially pure substance is a metal.

4. A burning oven according to claim 1, wherein said further material is formed from a ceramic layer.

5. A burning oven according to claim 1, wherein said substance is selected from the group consisting of silver, aluminum, gold, magnesium, and zinc.

6. A burning oven according to claim 1, wherein said calibrating device (26), is disposed approximately centrally in the middle of the oven.

7. A burning oven according to claim 1, wherein an automatic adjustment device (30) is provided in said burning oven (10), and wherein by means of said adjustment device said calibrating device (26) adjusts said temperature detection element (12) at a plurality of temperatures.

8. A burning oven according to claim 7, wherein said temperature sensor (28), by said calibration via the given number of temperature points, determines a temperature offset of said calibrating device (26) which offset is stored until a subsequent calibration.

9. A burning oven according to claim 1, wherein said calibrating device (26) is embodied as a retrofittable device for a burning oven.

\* \* \* \* \*